United States Patent [19]

Krauss et al.

[11] Patent Number: 5,602,467
[45] Date of Patent: Feb. 11, 1997

[54] CIRCUIT FOR MEASURING ION CONCENTRATIONS IN SOLUTIONS

[75] Inventors: Mathias Krauss, Ammerbuch; Beate Hildebrandt, Muchow; Christian Kunath; Eberhard Kurth, both of Dresden, all of Germany

[73] Assignee: Fraunhofer-Gesellschaft zur Foerderung der angewandten Forschung e.V., Munich, Germany

[21] Appl. No.: 392,792

[22] PCT Filed: Aug. 4, 1993

[86] PCT No.: PCT/DE93/00690

§ 371 Date: Apr. 24, 1995

§ 102(e) Date: Apr. 24, 1995

[87] PCT Pub. No.: WO94/06005

PCT Pub. Date: Mar. 17, 1994

[30] Foreign Application Priority Data

Aug. 28, 1992 [DE] Germany ............... 42 28 609.3

[51] Int. Cl.⁶ ................................................. G01R 27/26
[52] U.S. Cl. ........................................ 324/71.1; 327/307
[58] Field of Search ........................... 327/307; 324/439, 324/71.1, 71.6; 204/416

[56] References Cited

U.S. PATENT DOCUMENTS 4,385,274  5/1983  Shimada et al. ................. 324/71.6
4,754,169  6/1988  Morris .............................. 327/307

FOREIGN PATENT DOCUMENTS 2516656  5/1983  France .
3216791  12/1982  Germany .
3827314  10/1989  Germany .
2166904  5/1986  United Kingdom .

Primary Examiner—Maura K. Regan
Attorney, Agent, or Firm—Evenson, McKeown, Edwards & Lenahan, P.L.L.C.

[57] ABSTRACT

A circuit layout for measuring ion concentrations in solutions using ion-sensitive field effect transistors is provided. The circuit layout makes it possible to represent the threshold voltage difference of two ISFETs directly and independently of technological tolerances, operationally caused parameter fluctuations, and ambient influences. The circuit layout includes two measuring or test amplifiers, with in each case two differently or identically sensitive ISFETs and two identical FETs. The ISFETs and FETs are connected in such a manner that at the output of the first measuring amplifier occurs the difference of the mean value of the two ISFET threshold voltages and the FET threshold voltage and at the output of the second measuring amplifier occurs the difference of the two ISFET threshold voltages. The output of the first amplifier is connected to the common reference electrode of the four ISFETs.

13 Claims, 1 Drawing Sheet

CIRCUIT FOR MEASURING ION CONCENTRATIONS IN SOLUTIONS

BACKGROUND AND SUMMARY OF THE INVENTION

The invention relates to a circuit layout for measuring ion concentrations in solutions using ion-sensitive field effect transistors (ISFETs).

There is an increasing need for circuit layouts for determining ion concentrations and, in particular in the biomedical field, circuit layouts which can be integrated into a very small space are required, for example, for performing measurements on blood or urine.

The function of chemical sensors, on the basis of ion-sensitive field effect transistors, is based on the change to the threshold voltage of an ISFET as a function of the ion concentration in liquid electrolytes. The function of a circuit layout for determining the ion concentration with ISFETs is therefore limited to a threshold voltage measurement. The difficulty encountered is, inter alia, that with real ISFETs the desired sensor signal also has a strong dependence on different ambient influences and is also influenced by threshold voltage drifts caused by age.

A widely used method for determining the ion concentration in solutions is to measure the threshold voltage difference between an ISFET and a reference MOSFET, which operate in a negative feedback differential amplifier configuration. However, with this method it is only possible to compensate the parasitic threshold voltage influences, which are caused by the MOSFET configuration, so that, for example, external influences acting differently on the MOSFET and ISFET lead to erroneous measurements (operating point dependence of the threshold voltage). It is also disadvantageous that the known circuit layout can only operate in a narrow range around the prescribed operating point, so that it is not possible to compensate technological and operationally caused parameter fluctuations. Much better results can be obtained if the threshold voltage difference of two ISFETs having different sensitivities is evaluated. The use of ISFETs having different sensitivities presupposes the technical control of differently sensitive layers during the manufacturing process (cf. e.g. Isemi Igarashi et al: Multiple Ion Sensor Array, Sensors and Actuators, B1 (1990), pp.8–11). The measurement of this threshold voltage difference is not possible in the above-described manner in a simple differential amplifier, because the two ISFETs have a common gate connection in the electrolytic solution.

The subtract amplifier configuration described by A. Sibbald: A Chemical-Sensitive Integrated Circuit: The Operational Transducer, Sensors and Actuators, 7, 1985, pp.23–28 and specifically described on page 27 therein, suffers from the disadvantage that further circuit-caused quantities enter into the measured result and that it is necessary to calculate back from the output signal of the circuit, via the operating point current, to the actual sensor signal. Another disadvantage is that the two FETs are necessarily operated at different operating points, so that ambient influences cannot be compensated with the circuit.

German Patent document DE-A-3 216 791 discloses a circuit layout for measuring the ion concentration using ISFETs with different sensitivities. In this reference, the drain current of the ISFETs is kept constant by readjusting the gate voltage and the necessary voltage change for this is evaluated. However, the proposed circuit layout suffers from the disadvantage that disturbance variables, which can, for example, be caused by the amplifier or by operationally caused or technological tolerances, cannot be compensated. The prerequisite necessary for the error-free function of the circuit layout, i.e., that the difference in the transconductances of the ISFETs must be constant, cannot be ensured in the case of real ISFETs, so that this gives rise to an additional error source.

There is therefore needed a circuit layout with which it is possible to make available the threshold voltage difference of two ISFETs, having either the same or different sensitivities, for the ionic species to be measured in a direct manner independently of technologically caused tolerances, operationally caused parameter fluctuations and ambient influences. The threshold voltage difference should be made available as an analog output voltage, thus making it possible to test ISFETs for identical parameters.

According to the present invention, these needs are met by a circuit configuration formed from two measuring or test amplifiers. In the input stages of each of the measuring amplifiers, two ISFETs and two identical FETs are connected in such a manner so that the output voltage of the first measuring amplifier corresponds to the difference between the mean value of the two ISFET threshold voltages and the FET threshold voltage and the output voltage of the second measuring amplifier corresponds to the difference of the two ISFET threshold voltages of the amplifier. Thus, at the output of the first measuring amplifier there is always the offset voltage of the overall circuit layout. This offset voltage can be time-varied, for example, on the basis of external influences. By connecting the output of the first measuring amplifier to the common reference electrode of the four ISFETs, the operating point of the second measuring amplifier is fixed. Thus, the subtraction in the second measuring amplifier always takes place symmetrically to the operating point fixed by the first measuring amplifier. The output voltage of the second measuring amplifier represents the sensor signal, i.e. the threshold voltage difference between two ISFETs, and for an error-free measurement the ISFETs and FETs of the first measuring amplifier must be identical to those of the second amplifier. The FETs used in this circuit can, for example, be MOSFETs.

With the circuit layout according to the present invention, it is possible to directly make available the threshold voltage difference of two ISFETs, i.e., for example, without any additional computing expenditure, as an analog output voltage. As the operating point of the second measuring amplifier is determined by the output of the first amplifier, subtraction automatically takes place symmetrically to the set operating point in all cases. Therefore, the measurement by the circuit layout according to the present invention is advantageously independent of technologically caused tolerances of components, age-caused threshold voltage drifts, or fluctuations to operating parameters, such as temperature or operating voltage changes. The circuit layout according to the invention can also, for example, in the form of a CMOS circuit, be integrated into a modified standard process together with the ISFET sensors on a single chip, so that consequently measurements are possible in a highly confined space.

In a particularly advantageous embodiment of the circuit layout according to the present invention, two ISFETs having different sensitivities are used in the input stages of each of the two measuring amplifiers for the ionic species to be measured. This circuit layout makes it possible to link the advantages when determining the ion concentration with differently sensitive ISFETs with the aforementioned advantages of the circuit layout according to the invention.

A further advantageous embodiment of the circuit layout according to the present invention, in which there are two identically sensitive ISFETs in the input stages of the two measuring amplifiers, makes it possible to determine local concentration differences in an electrolytic solution (e.g. in a capillary).

During the measurement, the two ISFETs of the second measuring amplifier are separately positioned at two different locations in the solution to be measured. The two ISFETs of the first measuring amplifier, for example, together with the reference electrode, can be centrally positioned between the positions of the two ISFETs of the second measuring amplifier. If the ion concentrations at the two locations of the ISFETs of the second measuring amplifier are identical, then no voltage ($U \neq 0V$) is applied to the output of the circuit layout according to the invention. A corresponding output signal is obtained when concentration differences occur.

In a further preferred embodiment of the circuit layout according to the invention, the first measuring amplifier includes a known operational amplifier circuit, in which the input differential stage is replaced by a circuit layout of two differential amplifier stages. These differential amplifier stages in each case include a power source, a FET and an ISFET, which are connected in the following manner. The source connections of the FETs and ISFETs are in each case connected to the power source, the drain connections of the ISFETs to a load element common to both differential amplifiers, the drain connections of the FETs to a second load element common to both differential amplifiers and the gate connections of the two FETs to the reference potential, i.e., ground.

The connections of the load elements to the drain connections of the ISFETs and FETs are incorporated into the operational amplifier circuit so that emanating from the drain connections of the FETs and up to the output of the amplifier there is a negative sign of the gain and emanating from the drain connections of the ISFETs and extending up to the output of the amplifier there is a positive sign of the gain.

In a still further preferred embodiment of the circuit layout according to the invention, the second measuring amplifier includes a known operational amplifier circuit, in which the input differential stage is replaced by a circuit layout having two differential amplifier stages. These differential amplifier stages in each case comprise a power source, an FET and an ISFET, which are connected in the following manner. The source connections of the FETs and ISFETs are in each case connected to the power source, the drain connections of the ISFET of the first differential amplifier and the FET of the second differential amplifier to a common load element, and the drain connections of the FET of the first differential amplifier and the ISFET of the second differential amplifier to a second common load element. The gate connection of the first FET is connected to the reference potential, i.e., ground, and the gate connection of the second FET to the output of the amplifier.

The connections of the load elements to the drain connections of the ISFETs and FETs are incorporated into the operational amplifier circuit so that, emanating from a connection point of the first load element to the drain connections and extending to the amplifier output, there is a negative gain sign, and starting from the connecting point of the second load element to the drain connections and extending to the amplifier output, there is a positive gain sign.

According to a further embodiment, of the circuit layout according to the invention, use is made of FETs and ISFETs with the same layout. The four identical FETs are dimensioned in such a way that they have roughly the same transconductance as the four ISFETs. The four identical currents of the power sources are set so that the operating points of the ISFETs and FETs are well in the active range.

A preferred embodiment of the invention is obtained if MOSFETs are used as the field effect transistors (FETs).

According to a further embodiment of the circuit layout according to the invention, the currents of the power sources are made available by a bank of MOSFETs.

In another preferred embodiment of the circuit layout according to the invention, the reference electrode is made from an electrically good conducting material, which has a chemical resistance to the electrolytic solution, such as, for example, gold or platinum.

In a further embodiment according to the invention, the inventive circuit layout is in the form of a CMOS circuit and is integrated in a modified standard process together with the ISFETs on a single chip, so that the circuit layout permits measuring in a very confined space.

The circuit layout according to the present invention can be used for testing ISFETs. Whereas when using identical ISFETs at the same point in an electrolytic solution the threshold voltage difference is zero, differences of the ISFETs, which are, for example, due to technological parameter fluctuations during the manufacturing process, can be detected by a voltage ($U \neq 0V$) applied to the output of the circuit layout. It is therefore possible to test the ISFETs for identical parameters.

Other objects, advantages and novel features of the present invention will become apparent from the following detailed description of the invention when considered in conjunction with the accompanying drawings.

BRIEF DESCRIPTION OF THE DRAWING

The FIGURE is a schematic circuit diagram according to the present invention.

DETAILED DESCRIPTION OF THE DRAWING

Figure 1:
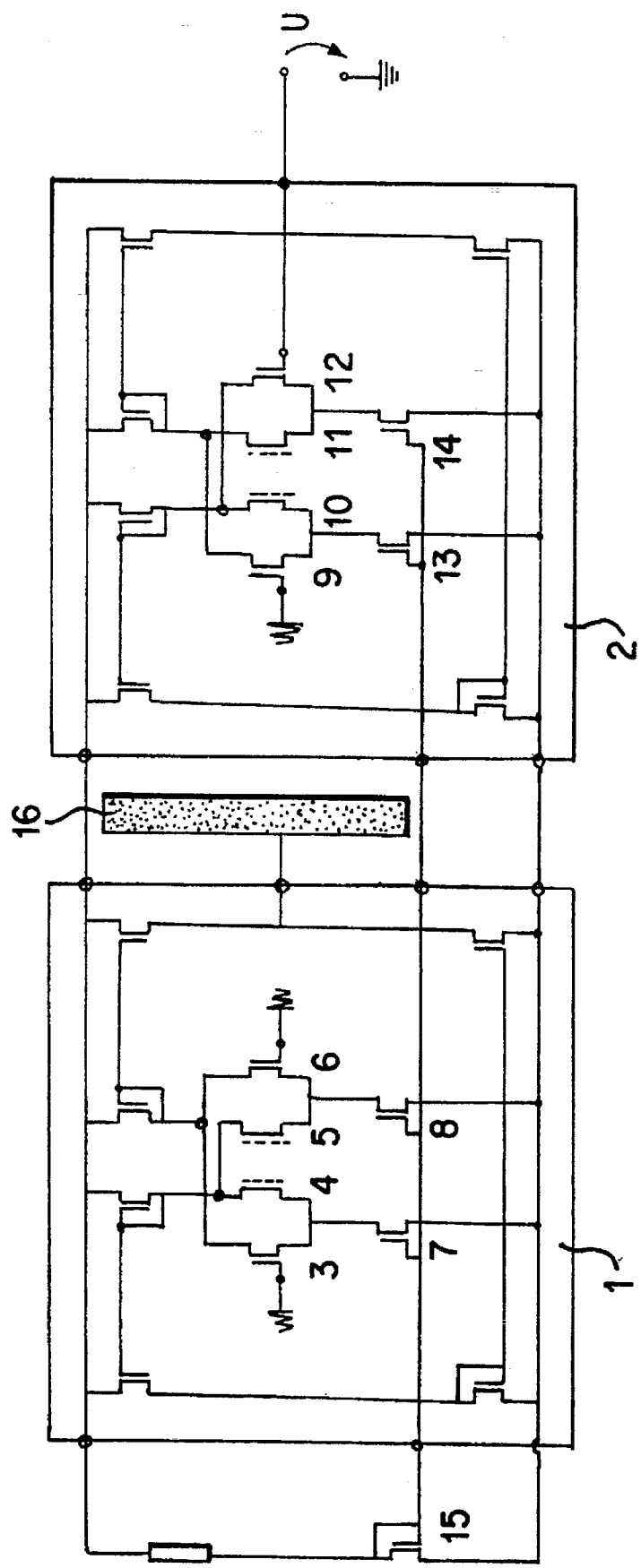

The circuit layout according to the present invention will now be explained in greater detail in an embodiment illustrated in the drawing FIGURE. The drawing FIGURE shows an example of a circuit layout according to the invention with two measuring or test amplifiers 1, 2 constructed in CMOS technology in accordance with the operational transconductance amplifier (OTA) principle. The currents for operating the two measuring amplifiers 1 and 2 are made available by a current bank of MOSFETs 7, 8, 13, 14 and 15. The amplifiers 1 and 2 only differ with respect to each other in regard to the connection of their input stages. With the input stage of the measuring amplifier 1, the difference is in the input and output-side parallel connection of two differential amplifiers of MOSFET 3 or 6 and ISFET 4 or 5, the two ISFETs 4 and 5 possibly having different sensitivities. The incorporation of the differential stages into the OTA circuit takes place in such a manner that the gates of the MOSFETs form the positive input of the amplifier configuration. The negative input of the amplifier is formed by the gates of the ISFETs, whose common electrical connection is formed by the electrode 16 located in the electrolytic solution. The electrodes can be formed from good conducting, chemically resistant, materials such as gold or platinum. By connecting the reference electrode 16 to the output of the measuring amplifier 1, the latter is fully feedback and operates as a voltage follower relative to the positive input, which is connected to the reference potential ground. Thus, the offset voltage of the overall layout appears at the output and, in the case of a largely symmetrical construction, the offset voltage assumes precisely the value of the difference of the threshold voltage of the MOSFETs and the mean value of the threshold voltages of the ISFETs.

In the measuring amplifier 2, the differential circuit layouts of MOSFET 9 or 12 and ISFET 10 or 11 are connected so that the gate connection of the MOSFET 9 forms a positive amplifier input and the gate of the MOSFET 12 a negative input. The reference electrode 16 once again represents the common electrical gate connection of the ISFETs 10 and 11. The gate connection is at the voltage regulated by the amplifier 1. From the signal standpoint, the reference electrode in the electrolytic solution forms a common-mode input for the amplifier 2. Through the negative feedback of the amplifier 2 as a voltage follower, and the connection of the positive input to reference potential, at its output is formed the threshold voltage difference resulting from the ISFETs 10 and 11. The threshold voltage difference corresponds to the measuring signal.

Through the choice of the operating point of the differential transistors 3 to 6 and 9 to 12 in the active range and due to the fact that the subtraction always takes place symmetrically to the common-mode operating point predetermined by the amplifier 1, it is ensured that the nonlinearities due to the square characteristics are adequately suppressed. This makes it possible to keep the sensor output signal error below 0.5° O even in the case of transconductance differences of up to 30 between the ISFET and MOSFET.

Although the invention has been described and illustrated in detail, it is to be clearly understood that the same is by way of illustration and example, and is not to be taken by way of limitation. The spirit and scope of the present invention are to be limited only by the terms of the appended claims.

We claim:

1. Circuit for measuring ion concentrations in solutions using ion-sensitive field effect transistors (ISFETs), a common reference electrode in the solution, and an output providing a sensor signal, the circuit comprising:
   two measuring amplifiers;
   two ISFETs and two identical FETs connected in an input stage of each of said two measuring amplifiers in such a manner that an output voltage of the first measuring amplifier corresponds to a difference of a mean value of a threshold voltage of said two ISFETs and an FET threshold voltage, and an output voltage of the second measuring amplifier corresponds to a difference of the threshold voltages of said two ISFETs, in which the two FETs and two ISFETs of the first measuring amplifier are identical to those of the second measuring amplifier, the output voltage of the first amplifier being connected to a common reference electrode of all of the ISFETs and the output voltage of the second amplifier corresponding to said sensor signal.

2. Circuit layout according to claim 1, wherein the two ISFETs of each measuring amplifier have different sensitivities.

3. Circuit layout according to claim 1, wherein the two ISFETs of each measuring amplifier have the same sensitivity.

4. Circuit layout according to claim 1, wherein the first measuring amplifier comprises an operational amplifier circuit, said operational amplifier circuit having an input differential stage formed of two differential amplifier stages, which in each case comprise a power source, as well as an FET and an ISFET, whose source connections are connected to the power source and whose drain connections are connected to two load elements common to both differential amplifiers, both FETs being connected to one load element and both ISFETs to the other load element, and wherein the gate connections of the two FETs are connected to reference potential and connecting points of the load elements to the drain connections being incorporated into the operational amplifier circuit so that, starting from the drain connections of the FETs and extending up to the amplifier output there is a negative gain sign and starting from the drain connections of the ISFETs and extending up to the amplifier output there is a positive gain sign.

5. Circuit layout according to claim 1, wherein the second measuring amplifier comprises an operational amplifier circuit, said operational amplifier circuit having an input differential stage formed from two differential amplifier stages, which in each case comprise a power source, as well as an FET and an ISFET, whose source connections are connected to the power source and whose drain connections are connected to two common load elements for both differential amplifiers, the FET of the first differential amplifier and the ISFET of the second differential amplifier being connected to the first load element, and the ISFET of the first differential amplifier and the FET of the second differential amplifier to the second load element, the gate connection of the first FET is connected to the reference potential, the gate connection of the second FET to the amplifier output, and the connections of the load elements to the drain connections being incorporated into the operational amplifier circuit so that, starting from the connection point of the first load element to the drain connections and extending to the amplifier output, a negative gain sign occurs and, starting from the connecting point of the second load element to the drain connections and extending up to the amplifier output, a positive gain sign occurs.

6. Circuit layout according to claim 4, wherein FETs and ISFETs with the same circuit layout are used, and wherein the four identical FETs are dimensioned so that they have substantially the same transconductance as the ISFETs and wherein the four identical currents of the power sources are selected so that the operating points of the ISFETs and FETs are in an active range.

7. Circuit layout according to claim 5, wherein FETs and ISFETs with the same circuit layout are used, and wherein the four identical FETs are dimensioned so that they have substantially the same transconductance as the ISFETs and wherein the four identical currents of the power sources are selected so that the operating points of the ISFETs and FETs are in an active range.

8. Circuit layout according to claim 1, wherein the FETs comprise MOSFETs.

9. Circuit layout according to claim 4, wherein the currents of the power sources are made available by a bank of MOSFETs.

10. Circuit layout according to claim 5, wherein the currents of the power sources are made available by a bank of MOSFETs.

11. Circuit layout according to claim 1, wherein the reference electrode is made from an electrically conducting, chemically resistant material.

12. Circuit layout according to claim 1, wherein the circuit layout is in the form of a CMOS circuit and, together with the ISFETs, is integrated on one chip.

13. Circuit layout according to claim 1, wherein said circuit layout is used for testing ISFETs for identical parameters.

* * * * *